United States Patent [19]

Elbe et al.

[11] Patent Number: 4,501,753
[45] Date of Patent: Feb. 26, 1985

[54] COMBATING PESTS WITH NOVEL SUBSTITUTED CARBAMOYLOXIMINO-TETRAHYDRO-THIOPHENES AND INTERMEDIATES THEREFOR

[75] Inventors: Hans-Ludwig Elbe, Wuppertal; Ingeborg Hammann, Cologne, both of Fed. Rep. of Germany

[73] Assignee: Bayer Aktiengesellschaft, Leverkusen, Fed. Rep. of Germany

[21] Appl. No.: 365,929

[22] Filed: Apr. 5, 1982

[30] Foreign Application Priority Data

Apr. 24, 1981 [DE] Fed. Rep. of Germany ....... 3116297

[51] Int. Cl.³ ..................... A01N 43/02; C07D 333/00
[52] U.S. Cl. ...................................... 514/447; 549/68
[58] Field of Search ........................... 549/68; 424/275

[56] References Cited

U.S. PATENT DOCUMENTS

| | | | |
|---|---|---|---|
| 3,317,562 | 5/1967 | Addor | 549/68 |
| 3,755,364 | 8/1973 | Magee | 549/68 |
| 4,232,035 | 11/1980 | D'Silva | 549/68 |

OTHER PUBLICATIONS

Frear Journal of Economic Entomology, vol. 39, (1946), pp. 736–741.

*Primary Examiner*—Alan Siegel
*Attorney, Agent, or Firm*—Sprung Horn Kramer & Woods

[57] ABSTRACT

Substituted carbamoyloximino-tetrahydrothiophenes or derivatives thereof of the formula

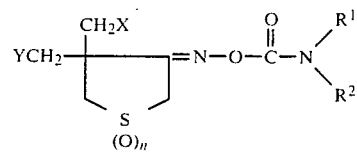

in which
  $R^1$ represents an alkyl, alkoxyalkyl, alkenyl or alkinyl group,
  $R^2$ represents a hydrogen atom, an alkyl group or a group of the general formula $-SR^3$ or $-S_2R^6$, wherein
  $R^3$ represents an alkyl, halogenoalkyl, optionally substituted phenyl, or alkoxycarbonyl group or a grouping of the general formula $-NR^4R^5$, or a radical which is identical to the rest of the molecule to which the group $-SR^3$ is bonded,
  $R^4$ represents an alkyl, alkoxycarbonyl or optionally substituted phenylsulphonyl group,
  X represents a hydrogen or halogen atom or a grouping of the general formula $-OR^5$ or $-SR^5$,
  Y represents a halogen atom or a grouping of the general formula $-OR^5$ or $-SR^5$,
  $R^5$ represents an alkyl group,
  $R^6$ represents an alkyl group or an optionally substituted phenyl group, and
  n is 0, 1 or 2, which possess pesticidal activity. The oximes from which they are made and the precursor ketones are also new.

8 Claims, No Drawings

COMBATING PESTS WITH NOVEL SUBSTITUTED CARBAMOYLOXIMINO-TETRAHYDROTHIOPHENES AND INTERMEDIATES THEREFOR

The present invention relates to certain new substituted carbamoyloxyimino-tetrahydrothiophenes and the derivatives thereof, to several processes for their production and to their use as pest-combating agents.

It has already been disclosed that 1-thia-3-aminocarbonyl-oximino-cyclopentanes, such as, for example, 1-thia-4,4-dimethyl-3-methyl-aminocarbonyl-oximino-cyclopentane, have pesticidal properties (see DE-AS (German Published Specification) 2,033,454). However, their action is not always completely satisfactory, particularly when low quantities are used.

The present invention now provides, as new compounds, the substituted carbamoyloximino-tetrahydrothiophenes, and the derivatives thereof, of the general formula

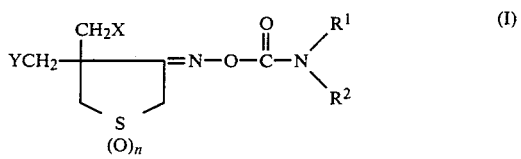

in which
R$^1$ represents an alkyl, alkoxyalkyl, alkenyl or alkinyl group,
R$^2$ represents a hydrogen atom, an alkyl group or a group of the general formula —SR$^3$ or —S$_2$R$^6$, wherein
R$^3$ represents an alkyl, halogenoalkyl, optionally substituted phenyl or alkoxycarbonyl group or a grouping of the general formula —NR$^4$R$^5$, or a radical which is identical to the rest of the molecule to which the group —SR$^3$ is bonded,
R$^4$ represents an alkyl, alkoxycarbonyl or optionally substituted phenylsulphonyl group,
X represents a hydrogen or halogen atom or a grouping of the general formula —OR$^5$ or —SR$^5$,
Y represents a halogen atom or a grouping of the general formula —OR$^5$ or —SR$^5$,
R$^5$ represents an alkyl group,
R$^6$ represents an alkyl group or an optionally substituted phenyl group, and
n is 0, 1 or 2.

The compounds of the formula (I) according to the present invention can be present in the syn form and anti form; they are predominantly produced as mixtures of the two forms.

According to the present invention we further provide a process for the production of a compound of formula (I) according to the present invention characterized in that (a) an oxime of the general formula

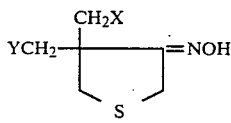

in which
X and Y have the meaning given above is reacted with a carbamoylating agent, preferably (a$_1$) with an isocyanate of the general formula

in which
R$^1$ has the meaning given above, in the presence of a diluent and, if appropriate, in the presence of a catalyst, or
(a$_2$) with a carbamoyl halide of the general formula

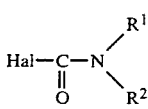

in which
R$^1$ and R$^2$ have the meanings given above and
Hal represents a fluorine, chlorine or bromine atom, in the presence of a diluent and of an acid-binding agent, or (b) if desired, the carbamoyloximino-tetrahydrothiophenes, obtained according to the reaction variant (a), of the general formula

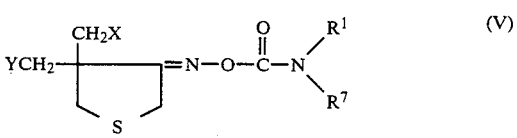

in which
R$^1$, and Y have the meanings given above and
R$^7$ represents a hydrogen atom or an alkyl group having 1 to 4 carbon atoms,
is oxidized to give a compound of the formula (I) with n=1 or n=2, depending on the oxidizing agent used, or (c) if desired, the carbamoyloximino-tetrahydrothiophenes, obtained according to reaction variant (a) and (b), of the general formula

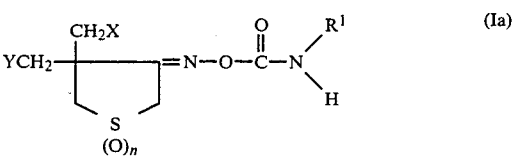

in which
R$^1$, X and Y have the meanings given above and
n is 0, 1 or 2,
are reacted with a sulphenyl chloride or bromide of the general formula

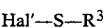

in which
R$^3$ has the meaning given above and
Hal' represents a chlorine or bromine atom,
in the presence of a diluent and of an acid-binding agent.

The present invention further provides, as new compounds, the oximes of the general formula

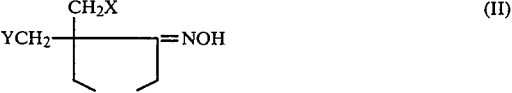

in which X and Y have the meanings given above.

According to the present invention we further provide a process for the production of an oxime of formula (II) according to the present invention characterized in that a ketone of the formula (VII)

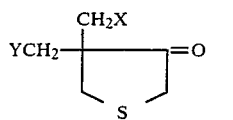 (VII)

in which X and Y have the meaning given above, is reacted with hydroxylamine, in the presence of a solvent, at a temperature between 20° and 100° C.

The present invention further provides, as new compounds, the ketones of the general formula

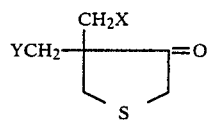 (VII)

in which X and Y have the meanings given above.

According to the present invention we further provide a process for the production of a ketone of the formula (VII) according to the present invention, characterized in that a halogeno-ketone of the general formula

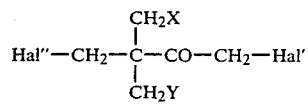 (VIII)

in which
Hal′, X and Y have the meanings given above and
Hal″ represents a chlorine or bromine atom,
is reacted with hydrogen sulphide or a metal hydrogen sulphide, in the presence of an organic solvent and in the presence of a base.

The new substituted carbamoyloximino-tetrahydrothiophenes of the formula (I) according to the present invention exhibit powerful pesticidal properties, particularly insecticidal and acaricidal properties. In this respect, the compounds also have a root systemic action. Surprisingly, the compounds according to the invention exhibit a higher degree of action in this respect than the known 1-thia-4,4-dimethyl-3-methyl-aminocarbonyloximino-cyclopentane, which is the most similar compound chemically and in terms of its action. The active compounds according to the invention thus represent an enrichment of the art.

Preferred substituted carbamoyloximino-tetrahydrothiophenes of formula (I) according to the invention are those
in which
$R^1$ represents a straight-chain or branched alkyl group having 1 to 4 carbon atoms, an alkoxyalkyl group having 1 to 4 carbon atoms in each alkyl part, or an alkenyl or alkinyl group, each having 2 to 4 carbon atoms,
$R^2$ represents a hydrogen atom, a straight-chain or branched alkyl group having 1 to 4 carbon atoms, or a group of the general formula —$SR^3$ or $S_2R^6$,
$R^3$ represents a straight-chain or branched alkyl group having 1 to 4 carbon atoms, a halogenoalkyl group having 1 or 2 carbon atoms and up to 5 halogen atoms (such as, in particular, fluorine atoms and chlorine atoms), an optionally substituted phenyl group, the substituent(s) thereon being selected from halogen (particularly fluorine, chlorine or bromine), alkyl having 1 or 2 carbon atoms and halogenoalkyl having 1 or 2 carbon atoms and up to 5 halogen atoms (such as, in particular, fluorine atoms and chlorine atoms) or represents an alkoxycarbonyl group having 1 to 4 carbon atoms in the alkyl part, or
$R^3$ additionally represents a grouping of the general formula —$NR^5R^4$, or a radical which is identical to the rest of the molecule to which the group —$SR^3$ is bonded,
$R^4$ represents an alkyl group having 1 to 4 carbon atoms, an alkoxycarbonyl group having 1 to 4 carbon atoms in the alkyl part or an optionally substituted phenylsulphonyl group, the substituent(s) being selected from those mentioned for $R^3$,
X represents a hydrogen, fluorine, chlorine or bromine atom or a grouping of the general formula —$OR^5$ or —$SR^5$,
Y represents a fluorine, chlorine or bromine atom or a grouping —$OR^5$ or —$SR^5$,
$R^5$ represents a straight-chain or branched alkyl group having 1 to 4 carbon atoms,
$R^6$ represents a straight-chain or branched alkyl group having 1 to 4 carbon atoms or an optionally substituted phenyl group, the phenyl substituent(s) being selected from those mentioned for $R^3$, and
n is 0, 1 or 2.

Very particularly preferred substituted carbamoyloximino-tetrahydrothiophenes of the formula (I) according to the present invention are those
in which
$R^1$ represents a methyl, ethyl, methoxymethyl or allyl group,
$R^2$ represents a hydrogen atom, a methyl or ethyl group or a group of the general formula —$SR^3$ or —$S_2R^6$,
$R^3$ represents a methyl, trifluoromethyl, chlorodifluoromethyl, dichlorofluoromethyl or trichloromethyl group, a phenyl group which is optionally substituted by chlorine or trifluoromethyl, a methoxycarbonyl or ethoxycarbonyl group or a grouping of the general formula —$N(CH_3)R^4$, or
$R^3$ represents a radical which is identical to the rest of the molecule to which the group —$SR^3$ is bonded,
$R^4$ represents a methyl, ethyl, methoxycarbonyl or ethoxycarbonyl group or a phenylsulphonyl group which is optionally substituted by chlorine or methyl,
X, Y and n have the meanings given immediately above,
$R^5$ represents a methyl or ethyl group, and
$R^6$ represents a methyl or ethyl group or a phenyl group which is optionally substituted by chlorine or trifluoromethyl.

In addition to the compounds mentioned in the preparative examples, the following compounds of the formula (I) may be individually mentioned:

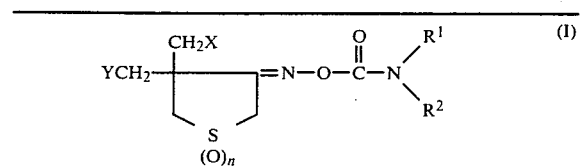 (I)

| X | Y | R¹ | R² | n |
|---|---|---|---|---|
| H | F | CH₃ | —SCCl₂F | 0 |
| H | Cl | CH₃ | —SCCl₂F | 0 |
| H | Br | CH₃ | —SCCl₂F | 0 |
| F | F | CH₃ | —SCCl₂F | 0 |
| Cl | Cl | CH₃ | —SCCl₂F | 0 |
| Br | Br | CH₃ | —SCCl₂F | 0 |
| H | F | CH₃ | —SCCl₃ | 0 |
| H | Cl | CH₃ | —SCCl₃ | 0 |
| H | Br | CH₃ | —SCCl₃ | 0 |
| Cl | Cl | CH₃ | —SCCl₃ | 0 |
| Br | Br | CH₃ | —SCCl₃ | 0 |
| F | F | CH₃ | —SCCl₃ | 0 |
| H | F | CH₃ | H | 0 |
| H | Cl | CH₃ | H | 0 |
| H | Br | CH₃ | H | 0 |
| F | F | CH₃ | H | 0 |
| Cl | Cl | CH₃ | H | 0 |
| Br | Br | CH₃ | H | 0 |
| H | Cl | CH₃ | —SCH₃ | 0 |
| H | Cl | CH₃ | 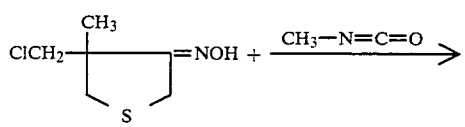 | 0 |
| H | Cl | CH₃ | —S—N(CH₃)—COOC₂H₅ | 0 |
| H | Cl | CH₃ | —S—N(CH₃)₂ | 0 |
| H | Cl | CH₃ | 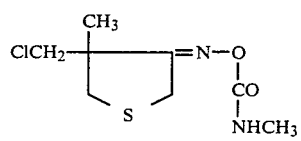 | 0 |
| H | Cl | CH₃ | —S—S—CH₃ | 0 |
| H | Cl | CH₃ | dimer | 0 |

If, for example, 4-chloromethyl-3-hydroximino-4-methyl-tetrahydrothiophene and methyl isocyanate are used as the starting materials, the course of the reaction variant (a) (process (a₁)) according to the present invention is illustrated by the following equation:

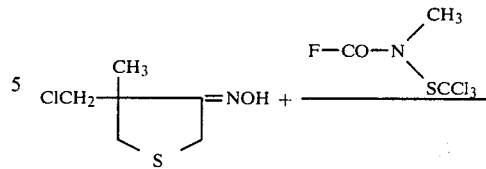

If, for example, 4-chloromethyl-3-hydroximino-4-methyl-tetrahydrothiophene and N-methyl-N-trichloromethylmercapto-carbamoyl fluoride are used as the starting materials, the course of the reaction variant (a) (process (a₂)) according to the present invention illustrated by the following equation:

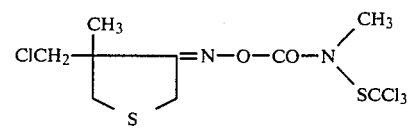

If, for example, 2 mols of 4-chloromethyl-3-hydroximino-4-methyl-tetrahydrothiophene and 1 mol of N,N'-bis-(fluorocarbonyl)-thio-bis-methylamine are used as the starting materials, the course of the reaction variant (a) (process (a₂)) with R² denoting —SR³ in which R³ denotes a radical which is identical to the rest of the molecule to which —SR³ is bonded) is illustrated by the following equation:

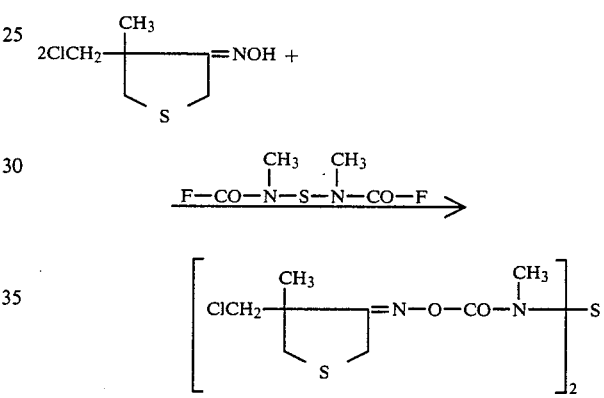

If, for example, 4-chloromethyl-4-methyl-3-methylcarbamoyl-oximino-tetrahydrothiophene is used as the starting material and hydrogen peroxide is used as the oxidizing agent, the course of the reaction variant (b) is illustrated by the following equation:

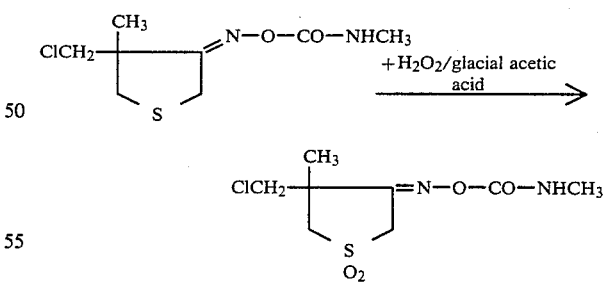

If, for example, 4-chloromethyl-4-methyl-3-methylcarbamoyl-oximino-tetrahydrothiophene and 4-chlorophenylsulfenyl chloride are used as the starting materials, the course of the reaction variant (c) is illustrated by the following equation:

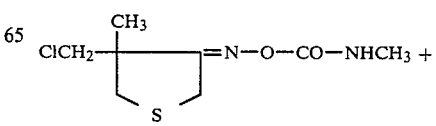

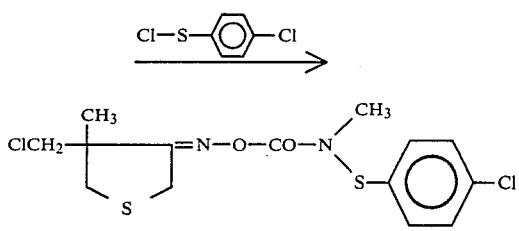

Preferred oximes of formula (II) to be used as starting materials for reaction variant (a) are those in which X and Y represent the radicals which have already been mentioned in this respect for the preferred compounds of the formula (I).

The oximes of the formula (II) are novel and form a further subject of the present invention.

The oximines of formula (II) are obtained, as mentioned previously, by a process according to the present invention in which a ketone of the general formula

in which X and Y have the meanings given above, is reacted with hydroxylamine in the presence of a solvent at a temperature between 20° and 100° C. In this reaction the solvent is preferably an alcohol or an aqueous alcohol and the temperature is preferably between 50° and 80° C. Also in this reaction, the hydroxylamine is preferably employed in the form of its salts (especially as the hydrochloride), in the presence of an acid-binding agent (such as sodium carbonate). The compounds of the formula (II) are isolated by working up according to customary methods, after the solvent has been distilled off, the product which forms during the reaction (see, also, the preparative examples).

The ketones of the formula (VII) are also novel and form a yet further subject of the present invention.

The ketones of formula (VII) are obtained, as mentioned previously, by a process according to the present invention in which a halogeno-ketone of the general formula

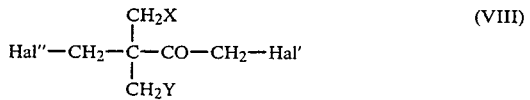

in which
Hal', X and Y have the meanings given above and
Hal" represents a chlorine or bromine atom, is reacted with hydrogen sulphide or a metal hydrogen sulphide in the presence of an organic solvent and in the presence of a base. In this reaction the metal hydrogen sulphide is preferably an alkali metal or alkaline earth metal hydrogen sulphide, the organic solvent is preferably methanol, and the base is preferably sodium methylate. The reaction is preferably carried out at a temperature between 0° and 100° C. (see, also, the preparative examples).

Some of the halogeno-ketones of the formula (VIII) are known (see, for example, U.S. Pat. No. 4,255,434 and U.S. Pat. No. 4,267,381 and can be obtained in a generally known manner.

Preferred isocyanates of formula (III) additionally required as starting materials for the process ($a_1$) according to the invention are those in which $R^1$ represents the radicals which have already been mentioned in this respect for the preferred and very particularly preferred compounds of the formula (I).

The isocyanates of the formula (III) are known or can be prepared according to generally customary and known processes.

Preferred carbamoyl halides additionally required as starting materials for the process ($a_2$) according to the invention are those in which $R^1$ and $R^2$ represent the radicals which have already been mentioned in this respect for the preferred and particularly preferred compounds of the formula (I).

The carbamoyl halides of the formula (IV) are known and can be prepared according to generally customary and known processes, for example by the reaction of amines with phosgene (these processes are known from general textbooks of organic chemistry), or by the reaction of the appropriate carbamic acid-halides with appropriate sulphenyl chlorides (in this connection also see the data in DE-AS (German Published Specification) 1,297,095, DE-OS (German Published Specification) 2,357,930 and 2,409,463, and U.S. Pat. No. 3,939,192).

Preferred sulphenyl chlorides or halides of formula (VI) further required as starting materials for reaction variant (c) are those in which $R^3$ represents the radicals which have already been mentioned in this respect for preferred and very particularly preferred compounds of the formula (I).

The sulphenyl chlorides or bromides are generally known compounds of organic chemistry.

Any of the inert organic solvents are preferred suitable diluents for the reaction according to processes ($a_1$) and ($a_2$) of reaction variant (a) and reaction variant (c). These include, as preferences, ketones, (such as diethyl ketone, and particularly acetone and methyl ethyl ketone), nitriles (such as propionitrile, and particularly acetonitrile), alcohols (such as ethanol or isopropanol), ethers (such as tetrahydrofuran or dioxane), formamides (such as, in particular, dimethylformamide), and halogenated hydrocarbons (such as methylene chloride, carbon tetrachloride or chloroform).

If the reaction according to process ($a_2$) and reaction variant (c) is carried out in the presence of an acid-binding agent, any of the inorganic and organic acid-binding agents which can customarily be used can be added. These include, as preferences, sodium carbonate, potassium carbonate and sodium bicarbonate, and also lower tertiary alkylamines, cycloalkylamines or aralkylamines (such as triethylamine, N,N-dimethyl-benzylamine, dicyclohexylamine, and also pyridine and diazabicyclooctane).

The following can be preferably used as catalysts in process ($a_1$): tertiary bases (such as triethylamine and pyridine) and organo-tin compounds (such as dibutyltin dilaurate).

In carrying out process ($a_1$), the reaction temperatures can be varied within a relatively wide range. In general, the reaction is carried out at a temperature between 0° and 100° C., preferably between 20° and 85° C. In carrying out process ($a_1$), 1 to 2 mols of isocyanate of the formula (III) are generally employed per mol of the compound of the formula (II). In order to isolate the compounds of the formula (I), the solvent is distilled off and the residue is worked up according to customary methods.

In carrying out process (a₂), the reaction temperatures can be varied within a relatively wide range. In general, the reaction is carried out at a temperature between 0° and 100° C., preferably between 10° and 80° C.

In carrying out process (a₂), 1 to 2 mols, in the case of a dimeric product, 0.5 mol, of carbamoyl halide of the formula (IV) and 1 to 2 mols of acid-binding agent are preferably employed per mol of the compound of the formula (II). The isolation of the compounds of the formula (I) is effected in a generally customary and known manner.

Suitable oxidizing agents for the reaction variant (b) are any of the inorganic and organic oxidizing agents which can customarily be used, such as chlorine in water, peracid (for example metachloroperbenzoic acid), hydrogen peroxide in glacial acetic acid or methanol, potassium permanganate and chromic acid.

In the oxidation according to reaction variant (b), the reaction temperatures can be varied within a relatively wide range. In general, the reaction is carried out at a temperature between −30° and +100° C., preferably at from −10° to +80° C.

In carrying out the oxidation according to reaction variant (b), 1 to 4 mols of oxidizing agent are generally employed per mol of the compound of the formula (V). When 1 mol of oxidizing agent (such as metachloroperbenzoic acid in methylene chloride or hydrogen peroxide in acetic anhydride) is used at a temperature between −10° and +10° C., the compounds according to the invention, of the formula (I), with n=1 are predominantly formed. With an excess of oxidizing agent and higher temperatures (10° to 80° C.), the compounds according to the invention, of the formula (I), with n=2 are predominantly formed.

In order to isolate the oxidation products, the reaction mixture is generally either poured onto ice water and filtered under suction, and the residual precipitate washed, if appropriate, and dried, or the reaction solution is adjusted to pH 7 to 8 and extracted with an organic solvent, and the extracted phase dried and the solvent distilled off. In both cases, the reaction products can be purified by recrystallization or column chromatography.

In carrying out reaction variant (c), the reaction temperatures can be varied within a relatively wide range. In general, the reaction is carried out at a temperature between 0 ° and 100° C., preferably between 10° and 50° C.

In carrying out reaction variant (c), the starting materials are preferably employed in molar quantities. The isolation of the compounds of the formula (I) is effected according to customary methods.

In some cases, it is also possible to carry out the individual stages of the precursors for the preparation of the oximes of the formula (II), as well as the reaction thereof to give the compounds according to the invention, without isolation of the particular intermediate products, in a so-called one-pot reaction.

The active compounds are well tolerated by plants, have a favorable level of toxicity to warm-blooded animals, and are suitable for combating arthropod pests, especially insects and arachnida, which are encountered in agriculture, in forestry, in the protection of stored products and of materials, and in the hygiene field.

They are active against normally sensitive and resistant species and against all or some stages of development.

The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisseliella, Tinea pellionella, Hofmannophila pseudospretella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., Tenebrio molitor, Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucillia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans and fumigating coils, as well as ULV cold mist and warm mist formulations.

These formulations may be produced in known-manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinylalcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 1% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular arthropods, especially insects or acarids) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATIVE EXAMPLES

EXAMPLE 1

(a) 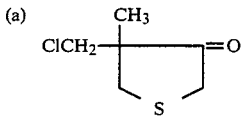

A 30% strength solution of 51 g (0.27 mol) of sodium hydrogen sulphide was added to 66.7 g (0.27 mol) of 1-bromo-4-chloro-3-chloromethyl-3-methyl-butan-2-one in 200 ml of methanol at 10° to 20° C. The reaction mixture was further stirred for 2 hours at 20° C. and was then added to water. The mixture was extracted with methylene chloride, the extracts were concentrated and the residue was distilled in vacuo. 35.4 g (80% of theory) of 4-chloromethyl-4-methyl-3-oxo-tetrahydrothiophene of refractive index $n_D^{20} = 1.5149$ were obtained.

(b) 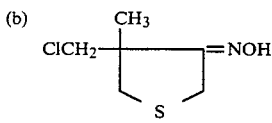

A solution of 13.1 g (0.188 mol) of hydroxylamine hydrochloride and 15.4 g of sodium acetate in 30 ml of water was added to 15.4 g (0.094 mol) of 4-chloromethyl-4-methyl-3-oxo-tetrahydrothiophene in 100 ml of methanol. The mixture was further stirred for 15 hours at 25° C. After the customary working-up of the reaction mixture and recrystallization from n-hexane, 11.8 g (70% of theory) of 4-chloromethyl-3-hydroximino-4-methyl-tetrahydrothiophene of melting point 86° to 87° C. were obtained.

(Process a₁)

(c) 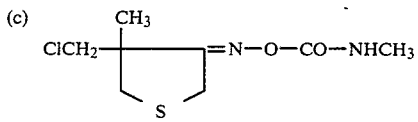

A solution of 10 g of methyl isocyanate in 20 ml of toluene was added to 10.2 g (0.057 mol) of 4-chloromethyl-3-hydroximino-4-methyl-tetrahydrothiophene in 180 ml of toluene at room temperature. The mixture was further stirred for 15 hours at room temperature. Dilute hydrochloric acid was then added to the reaction mixture, and the organic phase was separated off, washed with sodium bicarbonate solution, dried over sodium sulphate and concentrated in vacuo. 12.9 (96% of theory) of 4-chloromethyl-4-methyl-3-methylcarbamoyl-oximino-tetrahydrothiophene of melting point 103° to 105° C. were obtained.

EXAMPLE 2

(Process a₂)

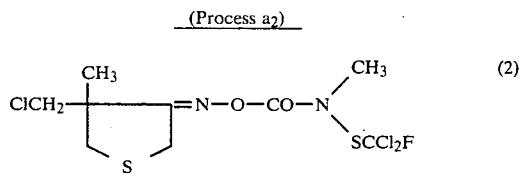

32.1 g (0.153 mol) of N-dichlorofluoromethylmercapto-N-methyl-carbamoyl fluoride in 80 ml of toluene were added to 27.4 g (0.153 mol) of 4-chloromethyl-3-hydroximino-4-methyl-tetrahydrothiophene at 15.5 g (0.153 mol) of triethylamine in 160 ml of toluene at room temperature. The mixture was further stirred for 4 hours at 40° C. After the customary working-up, 48.3 g (85% of theory) of 4-chloromethyl-4-methyl-3-(N-dichlorofluoromethylmercapto-N-methyl)-carbamoyl-oximino-tetrahydrothiophene of refractive index $n_D^{20} = 1.5460$ were obtained. Those compounds listed in the following table are obtained in a corresponding manner:

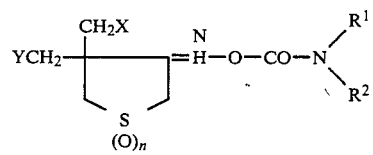

| Example Nr. | X | Y  | n | R¹  | R²         | Melting Point °C. |
|-------------|---|----|---|-----|------------|-------------------|
| 3           | H | Cl | O | CH₃ | dimer      | 40                |
| 4           | H | Cl | O | CH₃ | —SCCl₃     | 94                |
| 5           | H | Cl | O | CH₃ | —SN(CH₃)₂  | oil               |

The pesticidal activity of the compounds of this invention is illustrated by the following biotest examples.

In these examples the compounds according to the present invention are each identified by the number (given in brackets) from the corresponding preparative example. The known comparison compound is identified as follows:

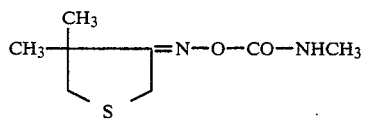

EXAMPLE A

Phaedon larvae test

Solvent: 3 parts by weight of dimethylformamide

Emulsifier: 1 part by weight of alkylaryl polyglycol ether

To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) were treated by being dipped into the preparation of the active compound of the desired concentration and were infested with mustard beetle larvae (*Phaedon cochleariae*), as long as the leaves were still wet.

After the specified periods of time, the destruction in % was determined. 100% meant that all the beetle larvae had been killed; 0% meant that none of the beetle larvae had been killed.

In this test, for example, the compound (1) showed a superior activity compared to the prior art.

EXAMPLE 8

Myzus test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (*Brassica oleracea*) which had been heavily infested with peach aphids (*Myzus persicae*) were treated by being dipped into the preparation of active compound of the desired concentration.

After the specified periods of time, the destruction in % was determined. 100% meant that all the aphids had been killed; 0% meant that none of the aphids had been killed.

In this test, for example, the compound (2) showed a superior activity compared to the prior art.

EXAMPLE C

Tetranychus test (resistant)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (*Phaseolus vulgaris*) which were heavily infested with the common spider mite or two-spotted spider mite (*Tetranychus urticae*) in all stages of development were treated by being dipped into the preparation of the active compound of the desired concentration.

After the specified periods of time, the destruction in % was determined. 100% meant that all the spider mites had been killed; 0% meant that none of the spider mites had been killed.

In this test, for example, the compound (2) showed a superior activity compared to the prior art.

It will be appreciated that the instant specification and examples are set forth by way of illustration and not limitation, and that various modifications and changes may be made without departing from the spirit and scope of the present invention.

I claim:

1. A substituted carbamoyloximino-tetrahydrothiophene, or derivative thereof, of the formula

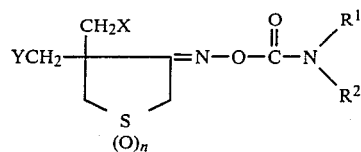

in which
 $R^1$ represents an alkyl, alkoxyalkyl, alkenyl or alkinyl group,
 $R^2$ represents a hydrogen atom, an alkyl group or a group of the general formula $-SR^3$ or $-S_2R^6$, wherein
 $R^3$ represents an alkyl, halogenoalkyl, optionally substituted phenyl or alkoxycarbonyl group or a grouping of the general formula $-NR^4R^5$, or a radical which is identical to the rest of the molecule to which the group $-SR^3$ is bonded,
 $R^4$ represents an alkyl, alkoxycarbonyl or optionally substituted phenylsulphonyl group,
 X represents a hydrogen or halogen atom or a grouping of the general formula $-OR^5$ or $-SR^5$,
 Y represents a halogen atom or a grouping of the general formula $-OR^5$ or $-SR^5$,
 $R^5$ represents an alkyl group,
 $R^6$ represents an alkyl group or an optionally substituted phenyl group, and
 n is 0, 1 or 2.

2. A compound according to claim 1, in which
 $R^1$ represents a straight-chain or branched alkyl group having 1 to 4 carbon atoms, an alkoxyalkyl group having 1 to 4 carbon atoms in each alkyl part, or an alkenyl or alkinyl group, each having 2 to 4 carbon atoms,
 $R^2$ represents a hydrogen atom, a straight-chain or branched alkyl group having 1 to 4 carbon atoms, or a group of the general formula $-SR^3$ or $-S_2R^6$,
 $R^3$ represents a straight-chain or branched alkyl group having 1 to 4 carbon atoms, a halogenoalkyl group having 1 or 2 carbon atoms and up to 5 halogen atoms, an optionally substituted phenyl group, the substituent(s) thereon being selected from halogen, alkyl having 1 or 2 carbon atoms and halogenoalkyl having 1 to 2 carbon atoms and up to 5 halogen atoms, or represents an alkoxycarbonyl group having 1 to 4 carbon atoms in the alkyl part, or
 $R^3$ additionally represents a grouping of the general formula $-NR^5R^4$, or a radical which is identical to the rest of the molecule to which the group $-SR^3$ is bonded,
 $R^4$ represents an alkyl group having 1 to 4 carbon atoms, an alkoxycarbonyl group having 1 to 4 carbon atoms in the alkyl part or an optionally substituted phenylsulphonyl group, the substituent(s) being selected from those mentioned for $R^3$,
 X represents a hydrogen, fluorine, chlorine or bromine atom or a grouping of the general formula $-OR^5$ or $-SR^5$,
 Y represents a fluorine, chlorine or bromine atom or a grouping $-OR^5$ or $-SR^5$,
 $R^5$ represents a straight-chain or branched alkyl group having 1 to 4 carbon atoms, and
 $R^6$ represents a straight-chain or branched alkyl group having 1 to 4 carbon atoms or an optionally substituted phenyl group, the phenyl substituent(s) being selected from those mentioned for $R^3$.

3. A compound according to claim 2, in which $R^1$ represents a methyl, ethyl, methoxymethyl or allyl group, $R^2$ represents a hydrogen atom, a methyl or ethyl group or a group of the general formula $-SR^3$ or $-S_2R^6$, $R^3$ represents a methyl, trifluoromethyl, chlorodifluoromethyl, dichlorofluoromethyl or trichloromethyl group, a phenyl group which is optionally substituted by chlorine or trifluoromethyl, a methoxycarbonyl or ethoxycarbonyl group or a grouping of the general formula $-N(CH_3)R^4$, or $R^3$ represents a radical which is identical to the reset of the molecule to which the group $-SR^3$ is bonded, $R^4$ represents a methyl, ethyl, methoxycarbonyl or ethoxycarbonyl group or a phenylsulphonyl group which is optionally substituted by chlorine or methyl, $R^5$ represents a methyl or ethyl group, and $R^6$ represents a methyl or ethyl group or a phenyl group which is optionally substituted by chlorine or trifluoromethyl.

4. A compound according to claim 1, wherein such compound is 4-chloromethyl-4-methyl-3-methylcarbamoyloximino-tetrahydrothiophene of the formula

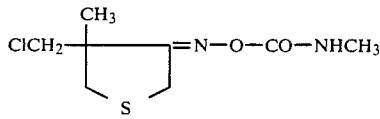

5. A compound according to claim 1, wherein such compound is 4-chloromethyl-4-methyl-3-(N-dichlorofluoromethylmercapto-N-methyl)-carbamoyl-oximino-tetrahydrothiophene of the formula

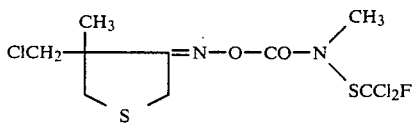

6. A pesticidal composition comprising a pesticidally effective amount of a compound according to claim 1 in admixture with a diluent.

7. A method of combating pests comprising applying to the pests, or to a habitat thereof, a pesticidally effective amount of a compound according to claim 1.

8. A method according to claim 7, wherein such compound is
    4-chloromethyl-4-methyl-3-methylcarbamoyl-oximinotetrahydrothiophene, or
    4-chloromethyl-4-methyl-3-(N-dichlorofluoromethylmercapto-N-methyl)-carbamoyl-oximino-tetrahydrothiophene,
and is applied to a domesticated animal to protect it from parasites.

* * * * *